United States Patent [19]

Small et al.

[11] Patent Number: 5,597,734

[45] Date of Patent: Jan. 28, 1997

[54] ION CHROMATOGRAPHY USING FREQUENT REGENERATION OF BATCH-TYPE SUPPRESSOR

[75] Inventors: Hamish Small, Leland, Mich.; John Riviello, Santa Cruz; Christopher A. Pohl, Union City, both of Calif.

[73] Assignee: Dionex Corporation, Sunnyvale, Calif.

[21] Appl. No.: 503,999

[22] Filed: Jul. 19, 1995

Related U.S. Application Data

[63] Continuation of Ser. No. 319,350, Oct. 6, 1994, abandoned, which is a continuation of Ser. No. 113,775, Aug. 27, 1993, abandoned.

[51] Int. Cl.$^6$ ................................................. G01N 30/02
[52] U.S. Cl. .................. 436/161; 210/656; 210/660; 210/662; 210/668; 436/150; 73/61.58; 73/61.61; 422/70
[58] Field of Search .................................. 436/161, 150; 422/70, 82.02, 90; 210/656, 660, 662, 668, 198.2; 73/61.58, 61.61

[56] References Cited

U.S. PATENT DOCUMENTS

| | | |
|---|---|---|
| 3,897,213 | 7/1975 | Stevens . |
| 3,920,397 | 11/1975 | Small . |
| 3,923,460 | 12/1975 | Parrott et al. . |
| 3,925,019 | 12/1975 | Small . |
| 3,926,559 | 12/1975 | Stevens . |
| 4,242,097 | 12/1980 | Rich, Jr. et al. ................. 422/70 |
| 4,265,634 | 5/1981 | Pohl . |
| 4,314,823 | 2/1982 | Rich, Jr. et al. . |
| 4,474,664 | 10/1984 | Stevens . |
| 4,751,004 | 6/1988 | Stevens et al. ................. 422/70 |
| 4,925,567 | 5/1990 | McAleese ....................... 422/70 |
| 4,999,098 | 3/1991 | Pohl . |
| 5,061,638 | 10/1991 | Guter ............................. 436/161 |

OTHER PUBLICATIONS

Hanaoka et al. "Ion Chromatography with an Ion Exchange Membrane Suppressor" J. Chromatography v. 239 pp. 537–548 (1982).
Jandik et al. "Electrochemical Detectors for Ion Chromatographic Analysis A Critical Review" Crit. Rev. Anal. Chem. 20(1) pp. 1–74 (1988).
Dasgupta, "Postcolumn Techniques: A Critical Perspective for Ion Chromatography" J. Chromatogr. Sci 27(8) pp. 422–448 (1989).
Pohl et al., "Ion Chromatography-The State-of-the-Art" J. Chrom. Sci vol. 18 pp. 442–452 (1980).
MacDonald, J., Ion Chromatography, American Laboratory, Jan. 1979, pp. 45–55.
Saari-Nordhaus et al., Solid Phase Chemical Suppression for Ion Chromatographic Analysis of Anions.
Gjerde, et al., Chromatographic Methods, Ion Chromatography, 2nd Ed.
Small, H., Ion Chromatography, Plenum Press, pp. 158–171 (No Date).
The Pittsburgh Conference, Mar. 8–12, 1993, Abstracts.
Saari-Nordhaus, R. et al., Ion Chromatographic Analysis of Anions Using a Solid-Phase Chemical Suppressor, American Laboratory, Jan. 1994, pp. 28C–28I.
Smith, F., et al., The Practice of Ion Chromatography, 1983, pp. 18–19.
Jupille, T. H. et al., Single–Column Ion Chromatography Aids Rapid Analysis, Reprint from Industrial Research & Development, Feb. 1983.

(List continued on next page.)

*Primary Examiner*—Jill Warden
*Assistant Examiner*—Jan M. Ludlow
*Attorney, Agent, or Firm*—Flehr, Hohbach, Test, Albritton & Herbert

[57] ABSTRACT

An ion chromatography method for analysis of a plurality of analyte ions in a sequence of samples in which ion chromatography is performed on a sample, which is passed to a non-precipitating suppressor ion exchange resin and analyzed, the suppressor being regenerated in one step prior to processing of a subsequent sample.

17 Claims, 4 Drawing Sheets

OTHER PUBLICATIONS

Stevens, Packed Fibers and New Columns Speed, Simplify Ion Chromatography, Sep. 1983.

Weiss, J., Handbook of Ion Chromatography, 1986, pp. 179–180.

Suden, et al., Separation of Sulfite, Sulfate, and Thiosulfate by Ion Chromatography with Gradient Elution; Anal. Chem. 1983, 55, pp. 2–4.

Small, H., Modern Inorganic Chromatography, Anal. Chem., vol. 55, Feb. 1983, pp. 235–242.

Villasenor, S., Matrix Elimination in Liquid Chromatography Using Heart–Cut Column Switching Techniques; Anal. Chem. 1991, 63, 1361–1366.

Hoover, T., et al., Determination of Trace Anions in Water my Multidimensional Ion Chromatography; Anal. Chem., 1984, 56, 221–225.

Rheodyne Incorporated Bulletin 114, Type 70 HPLC Switching Valves (No Date).

Valco Instruments Co. Inc. Catalog, 1993, pp. 10–17.

J. of Chromatog., 1981, v. 218, pp. 57–64.

J. of Chromatog., 1982, v. 237, pp. 297–302.

Ion Chromatography, Small, Hamish (Plenum Press, 1989) p. 187.

Suden, T., et al. Anal. Chem. 1984, v. 56, pp. 1085–1089.

Rocklin, R. D. et al. J. Chromatogr. v. 411 (1987) pp. 107–119.

ION CHROMATOGRAPHY USING FREQUENT REGENERATION OF BATCH-TYPE SUPPRESSOR

This is a continuation, of application Ser. No. 08/319,350 filed Oct. 6, 1994, now abandoned, which is a continuation of application Ser. No. 08/113,775, filed Aug. 27, 1993, now abandoned.

BACKGROUND OF THE INVENTION

The present invention relates to a method and apparatus using ion chromatography ("IC") followed by chemical conversion and detection of the sample ions.

Ion chromatography is a known technique for the analysis of sample in an eluent solution containing an electrolyte. The sample solution is injected into a chromatographic separation zone, in the form of an ion exchange column, and directed through an eluent suppression stage, and a detector, typically a conductivity detector. Ions of the injected sample are separated on and eluted from a separation column. In the suppression stage, electrical conductivity of the eluent electrolyte, but not that of the separated ions, is suppressed. This can be accomplished so long as the separated ions are not derived from very weak acids or bases and so can be determined by conductivity detection. This general technique is described in U.S. Draft Pat. Nos. 3,897,213, 3,920,397, 3,925,019 and 3,956,559. The above patents, incorporated herein by reference, describe suppression or stripping of electrolyte using an ion exchange resin bed device (called "a packed bed suppressor" or "PBS"). This general type of suppressor requires periodic shut-down for regeneration and performs in a batch rather than a continuous mode.

Disadvantages of the packed bed suppressor approach as it has been practiced are well documented. Such suppressors normally were run until the end of a shift or until exhaustion of the ion exchange resin, if earlier, followed by regeneration of the PBS. The PBS included a large volume of high capacity ion exchange resin. A typical ratio of the volume of the ion exchange resin in the suppressor to that of the separator column ranged from about 2.0 to 0.5 to one, thereby suppressing the developing reagents from a large number of separation runs (e.g. 15 to 50) prior to regeneration. Similarly, under such conditions, the ratio of capacity of the suppressor to that of the separation column was on the order of 100 to 700 to one.

Some disadvantages of the PBS approach are set forth in U.S. Pat. No. 4,474,604. For example, it limits the number of samples which can be consecutively analyzed. (Col. 1, lines 38–41). Also, certain difficulties are caused by the variable length of non-depleted resin in the column as it is being used up. This factor can vary elution times of certain ions, with less or no effect on other ions. (Col. 1, lines 50–55).

Other disadvantages of using a packed bed suppressor in the manner of the prior art include (1) restriction of the number of sample injections by the capacity of the suppressor, and (2) extra band spreading in the suppressor column resulting in lower resolution. (*J. of Chromatog.*, 1981, 218, 57, at 58). This is because the separated ionic species are re-mixed in the volume of the suppressor, resulting in a loss of resolution (peak broadening). The suppressor volume is thus a compromise between regeneration frequency and chromatographic resolution. Because of interaction with the suppressor column, the peak height of nitrite ion dramatically changes as a function of suppressor exhaustion. (*J. of Chromatog.*, 1982, 237, at 297).

An improved form of suppressor, called "a membrane suppressor", was developed to overcome these disadvantages. Significantly, the membrane suppressor is continuously regenerated during use, leading to its substantially replacing the packed bed suppressor. In a membrane suppressor, a charged membrane, normally in the form of a fiber or sheet, is used in place of the resin bed. In sheet form, the sample and eluent are passed on one side of the sheet with a flowing regenerant on the other side of the sheet. The sheet comprises an ion exchange membrane partitioning the regenerant from the effluent of chromatographic separation. The membrane passed ions of the same charge as the exchangeable ions of the membrane to convert the electrolyte of the eluent to a weakly ionized form, followed by detection of the ions. One highly effective form of suppressor is described in U.S. Pat. No. 4,999,098.

The membrane suppressor minimizes many of the foregoing disadvantages. However, membrane suppressors also have certain disadvantages compared to packed bed suppressors such as cost, leakage of regenerant causing higher detector background, the requirement for an external supply of regenerant solution and the fact that membrane suppressors are complex and not user serviceable. Thus, it would be advantageous to develop an inexpensive, high performance packed bed suppressor approach.

Gradient elution is performed by changing from a weak to a strong eluent during a chromatography run. Gradient elution has been attempted for the PBS approach. However, such attempts were "less than successful". (*Ion Chromatography*, Small, Hamish (Plenum Press, 1989, p.187) An attempt to solve one of the problems of such systems is set forth in Suden, T., et al. *Anal. Chem.* 1984, 56, 1085. Gradient elution also has been used in a membrane suppressor IC system. (See, e.g. Rocklin, R. D., et al. *J. Chromatogr.* 411 (1987) 107.

Gradient elution is particularly useful for analytes of interest having widely different affinities for the chromatographic stationary phase. An example in ion chromatography might be the separation of fluoride and citrate using anion exchange. In this case, fluoride has low affinity for the anion exchange column while citrate on the other hand has high affinity. In order to resolve these components in a single chromatographic analysis, gradient elution is used. In gradient elution, the elution process begins with an eluent of low displacing power than increases over time to an eluent of greater displacing power. This can be accomplished by changing the concentration and/or composition of the eluent. While gradient elution solves a variety of separation problems, detection can be a problem since the detector typically is sensing some property of the eluent. Suppression converts the eluent to a low conductivity form so that the conductivity detector in IC senses only very small changes in the background conductivity during the gradient elution process.

SUMMARY OF THE INVENTION

In accordance with the invention, ion chromatography methods and apparatus are provided using a batch-type suppressor (e.g. PBS) with significant advantages compared to (a) systems using PBS as performed in the prior art and (b) systems using membrane suppressors. The underlying principle is that certain advantages are obtained by frequent regeneration of a batch-type suppressor.

There are a number of different aspects of the present method. In one, the batch-type suppressor is regenerated after each chromatography run. First, the sample solution and electrolyte are separated and flow through the batch-type suppressor in which the electrolyte is converted to weakly ionized form and the analyte ions are converted to acid or base form. The effluent from this suppressor is detected. After a single run, the batch-type suppressor is regenerated by flowing a regenerant solution through it. Thereafter, the same steps are repeated for subsequent sample solutions.

In another aspect, regeneration occurs prior to substantial exhaustion of the batch-type suppressor, e.g. less than 50% exhausted. Here, one or more samples may be analyzed prior to regeneration so long as this limitation is met. Because of such frequent or sequential regeneration, much smaller capacity is required in the PBS compared to the prior art. A suitable relationship is that the capacity of the suppressor is not greater than about 10–20 times that of the separation medium. Capacity is defined as the number of milli-equivalents of ion exchange sites per ml of resin, times the volume of the column.

Analogously, the ratio of the volume of the ion exchange resin bed in the suppressor compared to the volume of the separating medium is small, e.g. is no greater than about 0.05 to 1. Volume is defined as the volume filled by the separating medium or medium in the PBS.

In yet another aspect, the frequency of regeneration may be defined in terms of the ratio of the time required to complete a single analysis (e.g. measured at the detector) versus the time required to regenerate the PBS. Suitably, such ratio is about 2:1 to 10:1, typically 3:1 to 5:1, compared to prior art where the ratio was on the order of 0.3:1 to 1:1.

Apparatus suitable for performing the present invention is similar to that of the prior art with the exception that very limited volume and capacity is required for the suppressor because of the frequent regeneration. Referring to the parameter of capacity, a ratio of total capacity of the ion exchange resin in the suppressor compared to that of the separating medium can be less than about 10–20 to 1. Defined in terms of volume, the ratio of the volume of the suppressor ion exchange resin compared to the volume of the separating medium may be less than about 0.05 to 1.

DETAILED DESCRIPTION OF THE PREFERRED EMBODIMENTS

The system of the present invention is useful for determining a large number of ionic species so long as the species to be determined are solely anions or solely cations. A suitable sample includes surface waters, and other liquids such as industrial chemical wastes, body fluids, beverages such as fruit juices and wines and drinking water.

When the term "ionic species" is used herein, it includes species in ionic form and components of molecules which are ionizable under the conditions of the present system.

"Exhaustion" is defined herein as complete conversion from the acid ($H_3O^+$) or base ($OH^-$) form, to the salt (e.g. $Na^+$ or $Cl^-$) form.

The term "batch-type suppressor" is defined as a flow-through channel in contact with ion exchange means capable of performing ion exchange suppression. In a typical batch-type suppressor, the ion exchange means is in the form of a bed (e.g. in the form of ion exchange resin), capable of suppression of the eluent electrolyte as described above. Such beds are referred to interchangeably by the terms "PBS" or "packed bed suppressor". Since such beds are a preferred form of batch-type suppressor, the present description will refer to the PBS. However, the term batch-type suppressor encompasses other ion exchange means which can perform the suppression function, e.g., a charged screen or ion exchange packing other than ion exchange resin or an ion exchange surface in contact with the channel. The term batch-type suppressor excludes membrane suppressors which operate continuously without shut-down for regeneration.

The purpose of the suppressor stage is to reduce the conductivity and noise of the analysis stream background while enhancing the conductivity of the analytes (i.e., increasing the signal/noise ratio) particularly for well ionized species, while maintaining chromatographic efficiency.

Figure 1A:
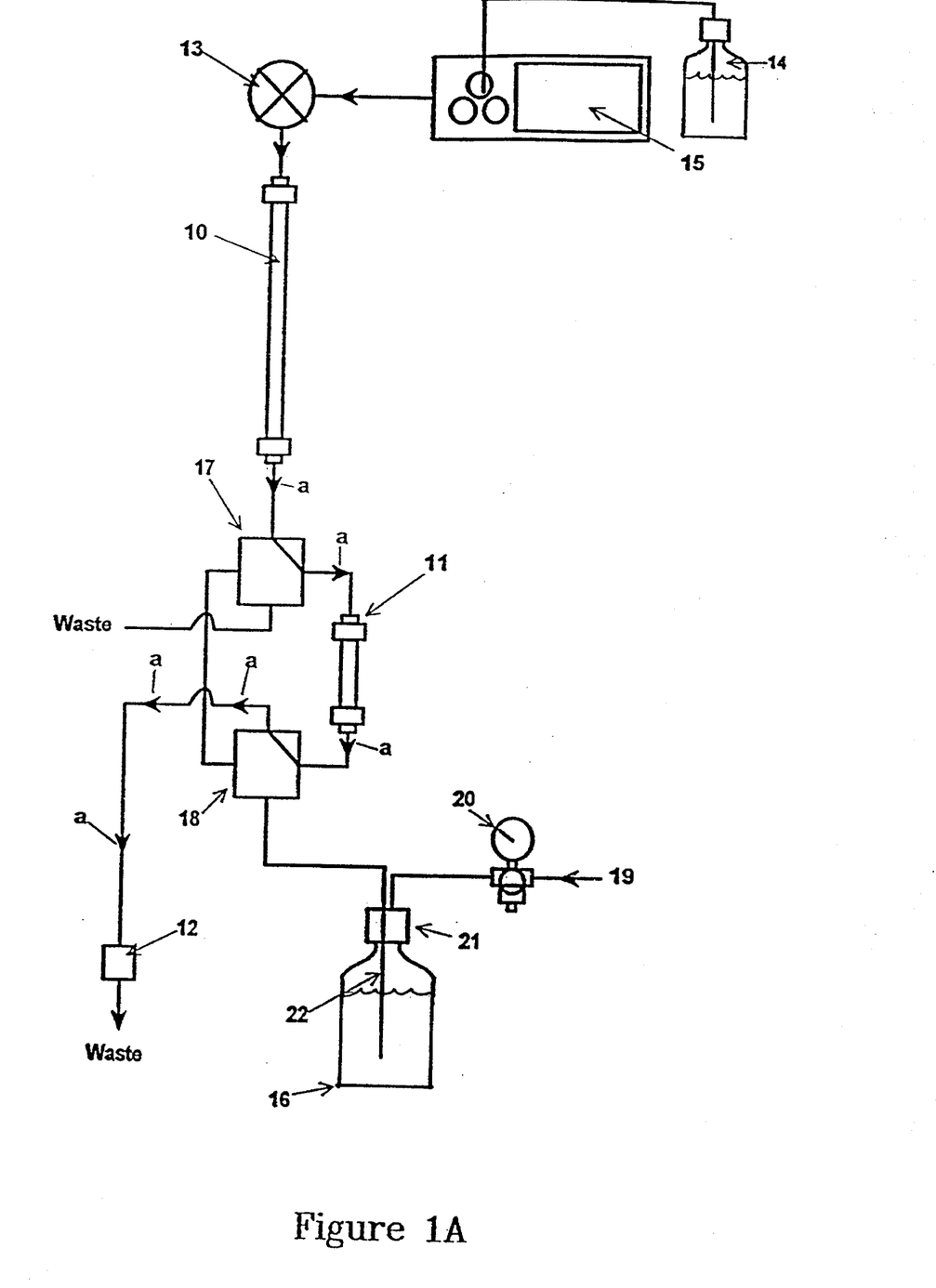
FIGS. 1A and 1B are schematic views of different valve settings for a system for performing ion chromatography according to the present invention using a single PBS.
Figure 1B:
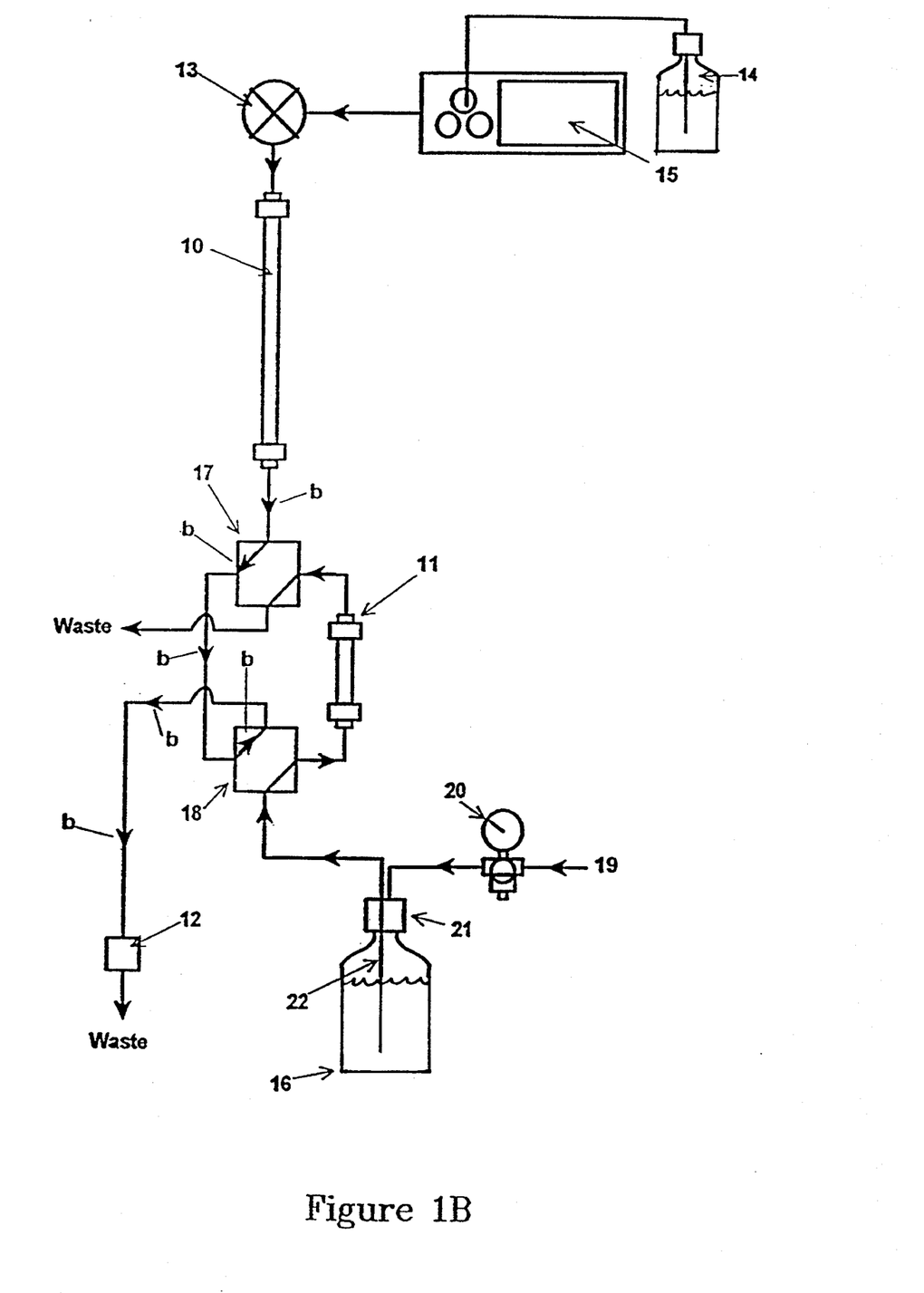

Referring to FIGS. 1A and 1B, a simplified apparatus for performing the present invention is illustrated. The system includes chromatographic separation means, typically in the form of a chromatographic separation column 10, which is packed with a chromatographic separation medium. In one embodiment referred to above, such medium is in the form of ion exchange resin. In another embodiment, the separation medium is a porous hydrophobic chromatographic resin with essentially no permanently attached ion exchange sites. This system is used for mobile phase ion chromatograph (MPIC) as described in U.S. Pat. No. 4,265,634. An ion exchange site-forming compound, including a hydrophobic portion and an ion exchange site, is passed through the column and is reversibly adsorbed to the resin to create ion exchange sites.

Arranged in series with column 10 is suppressor means 11 serving to suppress the conductivity of the electrolyte of the eluent from column 10 but not the conductivity of the separated ions. (This system works best for strong acids and strong bases.) The conductivity of the separated ions is usually enhanced in the suppression process.

The effluent from suppressor means 11 is directed to a first detector in the form of conductivity cell 12 for detecting all the resolved ionic species therefrom, preferably in the form of a flow-though conductivity cell. A suitable sample is supplied through sample injection valve 13 which is passed through the apparatus in the solution of eluent from eluent reservoir 14 drawn by pump 15, and then is passed through the sample injection valve 13. The solution leaving column 10 is directed to suppressor means 11 wherein the electrolyte is converted to a weakly conducting form.

The separated ionic species, treated by suppressor means 11, is then detected in the effluent. Means is provided for detecting the ion species. Preferably, detection is by ion conductivity and so the present system is described using an ion conductivity detector. However, other forms of detectors may be used including absorbance, mass spectrometry, and inductively coupled plasma. The detector of the present invention will be described with reference to conductivity detector 12.

Referring again to FIG. 1, the effluent from suppressor means 11 passed through conductivity cell 12. In conductivity cell 12, the presence of ionic species produces an electrical signal proportional to the amount of ionic material.

Such signal is typically directed from the cell 12 to a conductivity meter, not shown, thus permitting detection of the concentration of separated ionic species.

Means is provided for regenerating the PBS in the form of a regenerant reservoir 16. In one mode, to accomplish periodic regeneration of PBS 11, two cooperative three-way valves 17 and 18, respectively, are provided. Regenerant solution from a reservoir in the form of open-necked bottle 16 may be directed by any suitable means such as a pump or by gas pressure as from a nitrogen cylinder 19 through a pressure regulator 20 into the top of a stopper 21 in the neck of the bottle 16 taking the form of a fluid bottle.

Tubing 22 extends through the stopper 21 into the regenerant liquid in bottle 16 and receives the regenerant solution which is directed to valve 18.

FIG. 1A illustrates the valve setting for all stages except for regeneration. Specifically, the valve setting is the same for suppressor equilibration, the start of analysis and sample injection, and through the end of analysis. During all of these stages, valve 17 is set so that the effluent from column 10 flows through PBS 11, valve 18 and through conductivity cell 12 for analysis and then to waste. Arrows A illustrate the direction of the flow. In this valve setting, there is no flow in the regenerant line.

Referring to FIG. 1B, the valves are set for suppressor regeneration. The system is flushed by eluent flowing from the reservoir through valves 17 and 18 and to waste as illustrated by arrows B. During this cycle, the regenerant flows from reservoir 16 through valve 17, PBS 11, and through valve 17 to waste.

Figure 2A:
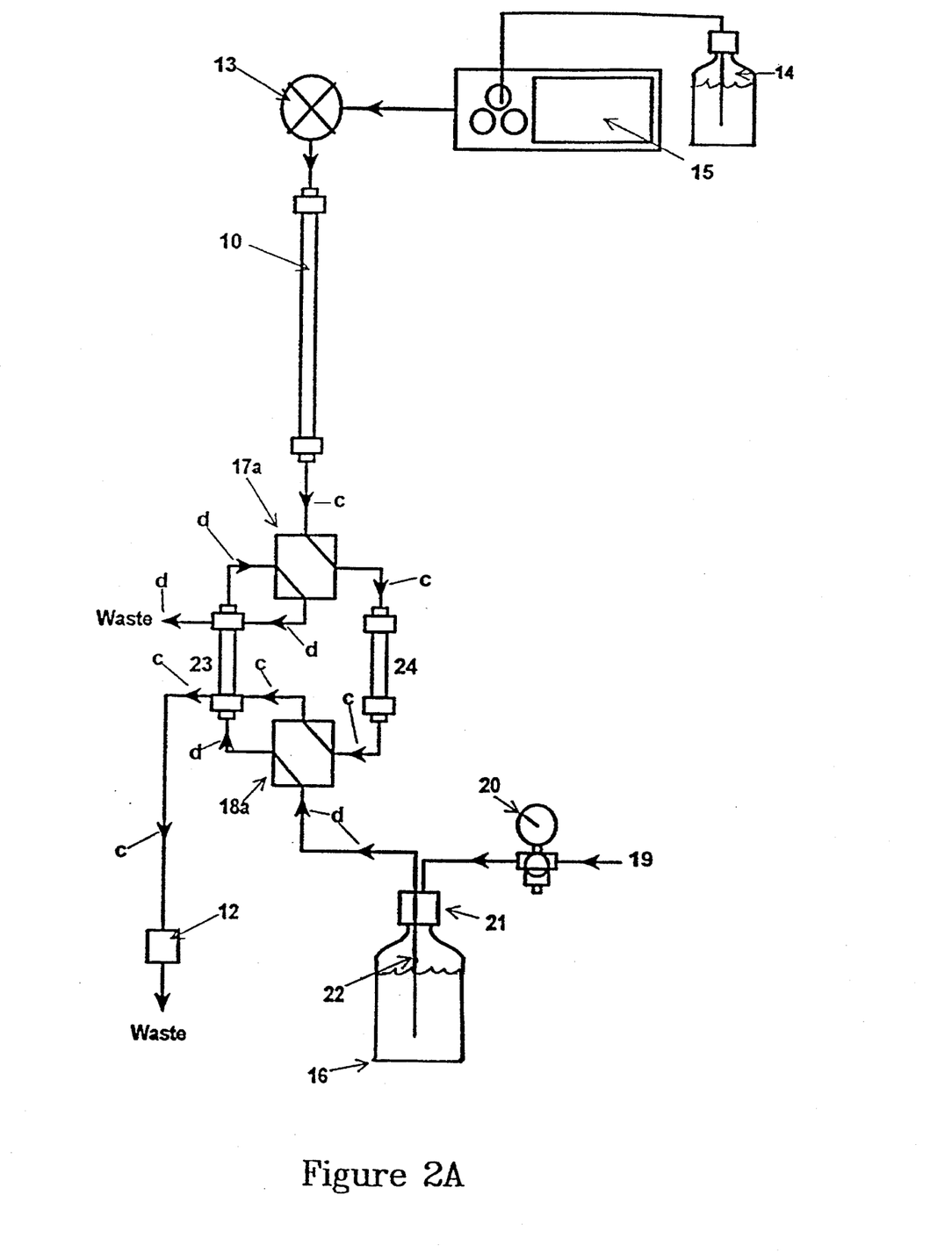
FIGS. 2A and 2B are schematic views of different valve settings for a system for performing the invention using two PBS's which are sequentially regenerated.
Figure 2B:
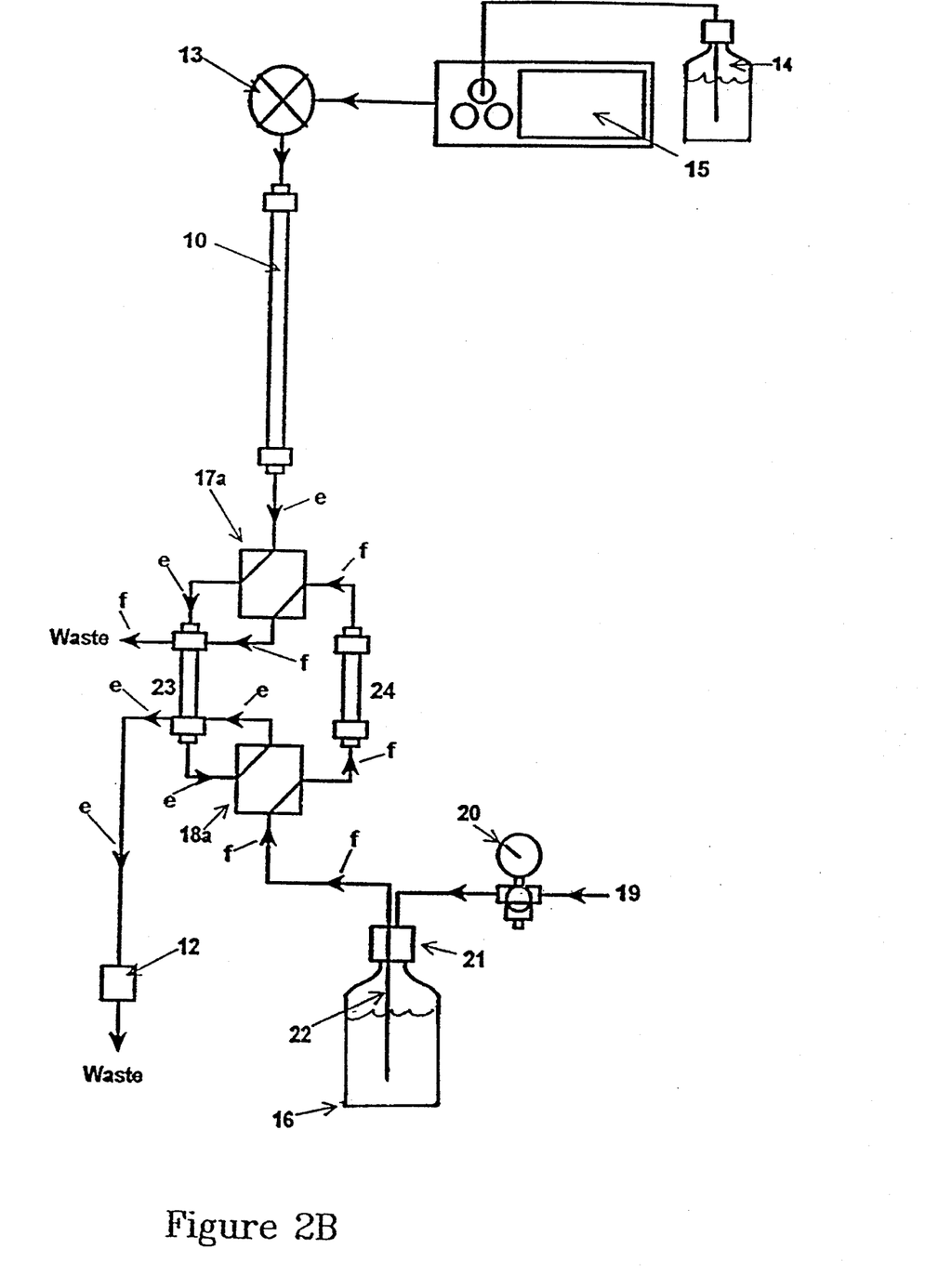

Referring to FIGS. 2A and 2B, the system is illustrated using two PBS's in which one PBS is being used while the other is being regenerated. Like parts will be designated with like numbers in the single PBS system of FIG. 1. In this instance, the suppressor to the right will be designated by the number 23 and the suppressor to the left will be designated by the number 24. In this case, two four-way valves, 17a and 18a, respectively are provided. The valve setting of FIG. 2A illustrates the use of suppressor 23 and regeneration of suppressor 24. Eluent flow is illustrated by the arrows C while regenerant flow is illustrated by the arrows D. Thus, the sample and analyte flow sequentially from analytical column 10, valve 17a, PBS 23, valve 18a, and through conductivity cell 12 in which the analyte ions are detected. Simultaneously, as indicated by arrow D, regenerant from reservoir 16 flows sequentially through valve 18a, PBS 24, valve 17a and to waste.

FIG. 2B illustrates the valve setting after completion of the cycle in which the valve setting is switched so that PBS 23 is being regenerated while PBS 24 is in use. In this instance, arrows E illustrate the flow of analyte ions for detection while arrows F illustrate the flow of regenerant through PBS 23.

Applicants have discovered that the combination of a small volume PBS and/or frequent regeneration of the PBS is advantageous in contradiction to the teachings of the prior art. These advantages include improved system efficiency due to lower suppressor column volume, no retention changes due to variable exclusion effects, and minimal undesirable chemical reactions due to resin contact. This enables the use of a micro-volume suppressor which can be regenerated after each analysis or after a few analyses in comparison to the large volume suppressors with less frequent regeneration. The ability to perform frequent regeneration and equilibration is unexpected. The analytical performance of the system with respect to detection limits, chromatographic efficiency and simplicity compare favorably with the membrane suppressor approach.

In one aspect of the invention, the PBS is regenerated after each chromatography run. Thus, after a typical analysis taking 5 to 15 minutes, illustrated in FIGS. 1A and 2A, the valving is switched to regenerate the PBS illustrated in FIGS. 1B and 2B. Suitable regeneration times are on the order of 1 to 5 minutes. A suitable ratio of analysis time to regeneration time to analysis time is 20:1 to 1:1 minutes. In other aspects of the invention described infra, one or more chromatography runs may be performed prior to regeneration.

In another aspect of the invention, the frequency of regeneration may be defined in terms of the time required to flow the sample solution through the analytical column or PBS. Typically, such flow prior to regeneration occurs in less than about 3 to 30 minutes compared to the much longer flow in the prior art PBS techniques. This interrelates with the low volume and low capacity PBS as set forth below.

Because of the frequent regeneration, the capacity of the PBS need be only a small fraction of the PBS capacity used in the prior art techniques which typically were run to exhaustion. In that regard, the ratio of total capacity of the ion exchange resin in the suppressor compared to that of the separator medium can be about 5 to 25 to 1 and is typically less than about 10 to 1. Defining this smaller capacity in terms of relative volumes, the ratio of the volume of the PBS ion exchange resin compared to the volume of the separating medium is typically from about 0.03 to 2 to 1, and, typically is less than about 0.05:1 to 1.

Equilibration of suppressor column typically takes about 1 to 5 minutes for an analysis of about 5 to 15 minutes. A suitable ratio of equilibration to analysis is from about 0.05:1 to 0.5:1. For a single PBS embodiment of FIG. 1, the ratio of analysis and equilibration time compared to regeneration time can be varied as desired. However, they are suitably performed in the same time.

For the dual PBS embodiment of FIG. 2, it is preferable that the analysis and equilibration time be equal to the regeneration time to use the illustrated cooperative valving. However, this timing may be varied by using other valve arrangements.

While a preferred mode is to regenerate after each cycle, two or more to as many as 5 analyses may be run, for certain applications, and still take advantage of the principle of frequent regeneration as set forth above.

In another aspect of the invention, the system may be defined in terms of the degree of exhaustion prior to regeneration. Thus, the PBS ion exchange resin is typically less than about 30% to 50% exhaustion prior to regeneration. This figure is significant in the context of the use of the relatively low capacity PBS of the present invention in comparison to the prior art.

The flow rates used for the described system are typical for ion chromatography. Also, the system is capable of analyzing the same type of analytes as analyzed in membrane suppressor systems using similar eluents including gradient eluents. Gradient elution is defined as elution performed by changing from a weak to a strong eluent during a run. Such an eluent is referred to as a gradient eluent. Examples of suitable gradient eluents are illustrated in Rocklin, R. D. et al (*Journal of Chromatography* 411 (1987) 107.) and in *Ion Chromatography*, Small, H. (Plenum Press 1989) pp. 187, 213. They include increases in eluent strength as a function of time in the shape of linear, concave, convex, step, linear with hold periods, and combinations of these functions.

The regenerant solution is similar to that used in the prior art. For example, the concentration of the regenerant suitably may be 0.01 to 3M and preferably 0.1 to 0.5M. The concentration to be used interrelates with the volume required which is typically small for this microvolume size of the PBS. For example, one mL of sulfuric acid as 0.3M is sufficient to regenerate a 2 mm×50 mm suppressor with a capacity of 0.2 meq per column.

In order to clearly define the invention, the following examples of its use are provided.

EXAMPLES

Example 1 — Isocratic Single PBS System

Chromatographic System:
  Instrument: Dionex DX-300 with AI 450 data collection and system control.
  Column: Dionex HPIC-AS4A SC
  Eluent: 1.8 mM $NaHCO_3$, 1.7 mM $Na_2CO_3$
  Eluent Flow rate: 2.0 mL/min.
  Sample
  1.
    1 mg/L $F^-$
    1.5 mg/L $Cl^-$
    1.5 mg/L $NO2^-$
    2.0 mg/L $Br^-$
    1.5 mg/L $NO_3^-$
    7.5 mg/L $HPO_4^{2-}$
    7.5 mg/L $SO_4^{2-}$
  2.
    266 ug/L $F^-$
    100 ug/L $Cl^-$
    100 ug/L $NO2^-$
    133 ug/L $Br^-$
    100 ug/L $NO_3^-$
    333 ug/L $HPO_4^{2-}$
    500 ug/L $SO_4^{2-}$
  Inj. Loop: 50 uL
Suppressor System:
  Column: 2 mm×50 mm hardware packed with Dowex 50×8 strong acid cation exchange resin.
  Regenerant: 0.3M H2SO4
  Regenerant Flow rate: 3 mL/min.
The following procedure is performed using the system of FIGS. 2A and 2B.

Step 1

Switch valve 17/18 so that eluent is by-passing suppressor column 11 and regenerant solution 16 is in line with suppressor column 11. Pump 0.3M $H_2SO_4$ regenerant (16) for 0.2 to 0.3 min. at 3 mL/min. by applying approximately 10 to 15 psi to regenerant bottle through regulator 20 from nitrogen source 19.

Step 2

Switch valve 17 back so that regenerant is not flowing through suppressor column and so that eluent is flowing from separator 10 through suppressor 11 and to detector cell 12.

Step 3

Allow the system to equilibrate. System is equilibrated when detector background drift is less than 0.03 uS/min. Equilibration takes typically 1 to 3 minutes.

Step 4

Load sample into injection valve 13 and inject sample into system. Collect chromatogram as detector response vs. time on a typical integrator or computer based chromatography data collection system.

FIG. 3 is a typical chromatogram collected from the single sequentially regenerated PBS system using Sample #1. FIG. 4 is an example of a chromatogram on the same system using sample #2, demonstrating minimal drift and excellent detection limits.

Example 2 — Isocratic, Dual SRPBS System

Chromatographic System:
  Instrument: Dionex DX-300 with AI 450 data collection and system control
  Column: Dionex HPIC-AS4A SC
  Eluent: 1.8 mM $NaHCO_3$, 1.7 mM $Na_2CO_3$
  Eluent Flow rate: 2.0 mL/min.
  Sample
    1 mg/L $F^-$
    1.5 mg/L $Cl^-$
    1.5 mg/L $NO_2^-$
    2.0 mg/L $Br^-$
    1.5 mg/L $NO_3^-$
    7.5 mg/L $HPO_4^{2-}$
    7.5 mg/L $SO_4^{2-}$
  Inj. Loop: 50 uL
Suppressor System:
  Column: 2 mm×50 mm hardware packed with Dowex 50X8 strong acid cation exchange resin.
  Regenerant: 0.3M H2SO4
  Regenerant Flow rate: 3 mL/min.
The following procedure is performed using the system of FIGS. 1A and 1B.

Step 1

Switch valve 17 so that eluent is flowing through suppressor column 23 and by-passing suppressor column 24 and regenerant solution 16 is flowing through suppressor column 11 and by-passing suppressor column 24. In this configuration, suppressor column 23 is in use and suppressor column 24 is positioned for regeneration.

Step 2

Pump 0.3M $H_2SO_4$ regenerant (16) for 0.2 to 0.3 min. at 3 mL/min. across suppressor column 23 by applying approximately 5 psi to regenerant bottle through regulator 20 from nitrogen source 19. Suppressor column 23 is being regenerated while suppressor column 24 is in use.

Step 3

While step 2 is in progress continue with steps 4 and 5.

Step 4

Allow the analytical system to equilibrate with the freshly regenerated suppressor column. System is equilibrated when detector background drift is less than 0.03 µS/min. Equilibration takes typically 1 to 3 minutes.

Step 5

Load sample into injection valve 13 and inject sample into system. Collect chromatogram as detector response vs. time on a typical integrator or computer based chromatography data collection.

Step 6

Switch valve 17 so that eluent is flowing through suppressor column 24 and by-passing suppressor column 23 and regenerant solution 16 is flowing through suppressor column 23 and by-passing suppressor column 24. In this configuration, suppressor column 24 is in use, and suppressor column 23 is positioned for regeneration.

Step 7

Continue with steps 2 through 5, alternating between freshly regenerated suppressors 23 and 24 for each sample injection.

Example 3—Gradient SRPBS System

Chromatography System:
  Instrument: Dionex DX-300 with AI 450 data collection and system control
  Column: Dionex HPIC-AS5A
  Eluent: 1 mM NaOH to 80 mM NaOH gradient in 30 min.
  Eluent Flow rate: 1.0 mL/min.
  Inj. Loop: 50 uL
  Sample:

| | | |
|---|---|---|
| 1. Fluoride | 1 mg/L |
| 2. Acetate | 10 mg/L |
| 3. Butyrate | 10 mg/L |
| 4. Formate | 5 mg/L |
| 5. Pyruvate | 10 mg/L |
| 6. Monochloroacetate | 10 mg/L |
| 7. Bromate | 10 mg/L |
| 8. Chloride | 10 mg/L |
| 9. Nitrite | 10 mg/L |
| 10. Dicloroacetate | 10 mg/L |
| 11. Selenite | 10 mg/L |
| 12. Bromide | 10 mg/L |
| 13. Nitrate | 10 mg/L |
| 14. Sulfate | 10 mg/L |
| 15. Oxalate | 10 mg/L |
| 16. Selenate | 10 mg/L |
| 17. Phosphate | 10 mg/L |
| 18. Arsenate | 10 mg/L |
| 19. Chromate | 10 mg/L |
| 20. Citrate | 10 mg/L |

Suppressor System:
  Column: 2 mm×250 mm hardware packed with Dowex 50×8 trong acid cation exchange resin.
  Reagent: 0.3M H2S04
  Regenerant Flow rate: 2 mL/min.
The following procedure is performed using the system of FIGS. 1A and 1B.

Step 1

Switch valve 17 so that eluent is by-passing suppressor column 11 and regenerant solution 16 is in line with suppressor column 11. Pump 0.3M $H_2SO_4$ regenerant (16) for 3 minutes at 2 mL/min. by applying approximately 10 to 15 psi to regenerant bottle through regulator 20 from nitrogen source 19.

Step 2

Switch valve 17 back so that regenerant is not flowing through suppressor column and so that eluent is flowing from separator 10 through suppressor 11 and to detector cell 12.

Step 3

Allow the system to equilibrate. System is equilibrated when detector background drift is less than 0.03 uS/min. Equilibration takes typically 1 to 3 minutes. The separator column requires approximately 5 to 15 minutes of equilibration with starting eluent to provide reproducible chromatography, thus the suppressor equilibrates with eluent during the same period.

Step 4

Load sample into injection valve 13 and inject sample into system. Start eluent gradient at the same time the sample is injected. Collect chromatogram as detector response vs. time on a typical integrator or computer based chromatography data collection system.

FIG. 5 is an example of a gradient chromatogram generated using the sample and method described.

What is claimed is:

1. An ion chromatography method for analysis of a plurality of analyte ions in a sequential flow of sample solutions, each analyte ion being of a common charge, said charge being one of positive or negative, said method comprising:
  (a) eluting at least one sample solution containing said analyte ions in the presence of an eluent comprising an electrolyte through separating medium effective to separate the analyte ions, thereby exiting as separation medium effluent,
  (b) flowing said separation medium effluent through an ion exchange resin bed suppressor containing ion exchange resin for suppressing said at least one sample solution, said electrolyte being converted to weakly ionized form by the non-precipitating ion retention on said suppressor ion exchange resin of the electrolyte ions of opposite charge to said analyte ions and said analyte ions being converted to acid or base form thereby exiting as a suppressor effluent,
  (c) analyzing said suppressor effluent by a detector to produce a first signal,
  (d) after completion of step (c), flowing a regenerant solution through said suppressor to regenerate in one step said suppressor ion exchange resin, the ratio of the time for step (c) to the time for step (d) being at least about 2:1, and
  (e) then, repeating steps (a)–(c) for at least a subsequent sample solution.

2. The method of claim 1 in which the ratio of the volume of the ion exchange resin bed in said suppressor compared to the volume of said separating medium is no greater than about 0.2 to 1.

3. The method of claim 1 in which the ratio of the total capacity of the ion exchange resin used in said suppressor compared to the total capacity of said separating medium is no greater than 25 to 1.

4. The method of claim 1 in which only one sample solution is eluted in the first performance of step (a) prior to step (d).

5. The method of claim 1 in which the ratio of step (d) is at least about 3:1.

6. The method of claim 1 in which the ratio of step (d) is at least about 5:1.

7. The method of claim 1 in which the regeneration of step (d) is performed in no greater than about 5 minutes.

8. The method of claim 1 in which the analysis of step (c) is performed in no greater than about 30 minutes.

9. An ion chromatography method for analysis of a plurality of analyte ions in a sequential flow of sample solutions, each analyte ion being of a common charge, said charge being one of positive or negative, said method comprising:

(a) eluting at least one sample solution containing said analyte ions in the presence of an eluent comprising an electrolyte through separating medium effective to separate the analyte ions, thereby exiting as separation medium effluent, (b) flowing said separation medium effluent through an ion exchange resin bed suppressor containing ion exchange resin for suppressing said at least one sample solution, in which the electrolyte is converted to weakly ionized form by the non-precipitating ion retention on said suppressor ion exchange resin of the electrolyte ions of opposite charge to said analyte ions and the analyte ions are converted to acid or base form, thereby exiting as a suppressor effluent, the ratio of the total capacity of the ion exchange resin in said suppressor compared to the total capacity of said separating medium being no greater than about 25 to 1, (c) analyzing said suppressor effluent by a detector to produce a first signal, (d) after completion of step (c), flowing a regenerant solution through said suppressor to regenerate in one step said ion exchange resin, and (e) repeating steps (a)–(c) for at least a subsequent sample solution.

10. The method of claim 9 in which the ratio of the volume of the ion exchange resin bed in said suppressor compared to the volume of said separating medium is no greater than about 0.2 to 1.

11. The method of claim 9 in which step (e) is repeated for a third and fourth sample in series.

12. The method of claim 9 in which the ratio of that capacity of the ion exchange resin in the suppressor compared to the capacity of the separating column is less than about 10:1.

13. An ion chromatography method for analysis of a plurality of analyte ions in a sequential flow of sample solutions, each analyte ion being of a common charge, charge being one of positive or negative, said method comprising:

(a) eluting at least one sample solution containing said analyte ions in the presence of an eluent comprising an electrolyte through separating medium effective to separate the analyte ions, thereby exiting as separation medium effluent, (b) flowing said separation medium effluent through an ion exchange resin bed suppressor containing ion exchange resin for suppressing said at least one sample solution said electrolyte being converted to weakly ionized form by the non-precipitating ion retention on said suppressor ion exchange resin of the electrolyte ions of opposite charge to said analyte ions and said analyte ions being converted to acid or base form, thereby exiting as a suppressor effluent, (c) analyzing said suppressor effluent for no greater than 30 minutes by a detector to produce a first signal, (d) after completion of step (c), flowing a regenerant solution in one step through said suppressor to regenerate said suppressor ion exchange resin, the ratio of the time for step (c) to the time for step (d) being at least 1:1, and (e) then, repeating steps (a)–(c) for at least a subsequent sample solution.

14. An ion chromatography method for analysis of a plurality of analyte ions in a sequential flow of sample solutions, each analyte ion being of a common charge, said charge being one of positive or negative, said method comprising:

(a) eluting a first sample solution containing said analyte ions in the presence of an eluent comprising an electrolyte through separating medium effective to separate the analyte ions, thereby exiting as separation medium effluent.

(b) flowing said separation medium effluent through a batch-type suppressor including ion exchange resin, said electrolyte being converted to weakly ionized form by the non-precipitating ion retention on said suppressor ion exchange resin of the electrolyte ions of opposite charge to said analyte ions and said analyte ions being converted to acid or base form, thereby exiting as a suppressor effluent, (c) analyzing said suppressor effluent using a detector to produce a first signal, (d) after completion of step (c), flowing a regenerant solution through said suppressor to regenerate in one step said ion exchange resin, (e) repeating steps (a)–(d) for a second sample solution.

15. The method of claim 14 in which the ratio of the total capacity of the ion exchange resin used in said suppressor compared to the total capacity of said separating medium is no greater than 25 to 1.

16. The method of claim 14 in which step (e) is repeated for a third and fourth sample in series.

17. The method of claims 1, 9, or 14, in which the elution of step (a) is performed by gradient elution using a gradient eluent.

* * * * *

UNITED STATES PATENT AND TRADEMARK OFFICE
CERTIFICATE OF CORRECTION

PATENT NO. : 5,597,734

DATED : January 28, 1997

INVENTOR(S) : Small, et al.

It is certified that error appears in the above-indentified patent and that said Letters Patent is hereby corrected as shown below:

At column 8, delete lines 13-17.

At column 10, delete lines 34-35.

Signed and Sealed this

Eighth Day of July, 1997

Attest:

BRUCE LEHMAN

*Attesting Officer*  *Commissioner of Patents and Trademarks*